United States Patent [19]
Marcolongo et al.

[11] Patent Number: 5,721,049
[45] Date of Patent: Feb. 24, 1998

[54] COMPOSITE MATERIALS USING BONE BIOACTIVE GLASS AND CERAMIC FIBERS

[75] Inventors: Michele S. Marcolongo, Lansdowne; Paul Ducheyne, Rosemont; Frank Ko, Philadelphia, all of Pa.; William LaCourse, Alfred, N.Y.

[73] Assignee: Trustees of the University of Pennsylvania, Philadelphia, Pa.

[21] Appl. No.: 463,009

[22] Filed: Jun. 5, 1995

Related U.S. Application Data

[60] Division of Ser. No. 436,585, May 8, 1995, which is a continuation-in-part of Ser. No. 152,962, Nov. 15, 1993, Pat. No. 5,468,544.

[51] Int. Cl.⁶ .......................... C04B 33/24; C03C 3/076; B32B 17/04

[52] U.S. Cl. .................. 428/370; 428/300.4; 428/357; 428/361; 428/373; 428/374; 428/411.1; 623/11; 623/16; 501/35; 501/55; 501/63; 501/68

[58] Field of Search .................. 623/11, 16; 501/35, 501/55, 63, 68; 433/201.1; 424/76.8; 106/35; 523/114; 524/443; 428/224, 247, 280, 411.1, 357, 361, 370, 373, 324

[56] References Cited

U.S. PATENT DOCUMENTS

| | | | |
|---|---|---|---|
| 4,131,597 | 12/1978 | Bluethgen | 260/42.18 |
| 4,202,055 | 5/1980 | Reiner et al. | 3/1.91 |
| 4,239,113 | 12/1980 | Gross et al. | 206/568 |
| 4,329,743 | 5/1982 | Alexander et al. | 3/1 |
| 4,411,027 | 10/1983 | Alexander et al. | 3/1 |
| 4,604,097 | 8/1986 | Graves, Jr. et al. | 623/11 |
| 4,781,183 | 11/1988 | Casey et al. | 128/92 YP |

OTHER PUBLICATIONS

P. Boone, et al., "Bone Attachment of HA Coated Polymers," *J. Biomed. Mater. Res.* 23, No. A2:183–199 (1989).

Gross et al., "The Response of Bone to Surface–Active Glasses/Glass–Ceramics", *CRC Critical Reviews in Biocompatibility*, 4, 155–179 (1988).

L. Hench, et al., "Bonding Mechanisms at the Interface of Ceramic Prosthetic Materials," *J. Biomed. Mater. Res.*, 2:117–141 (1971).

Hench, L.L., "Bioactive Glasses and Glass–Ceramics: A Perspective", *Handbook of Bioactive Ceramics, vol. 1*, T. Yamamuro, L.L. Hench, and J. Wilson, eds., pp. 7–23, CRC Press, Boca Raton (1990).

(List continued on next page.)

*Primary Examiner*—Patrick Ryan
*Assistant Examiner*—Rich Weisberger
*Attorney, Agent, or Firm*—Woodcock Washburn Kurtz MacKiewicz & Norris

[57] ABSTRACT

Composite materials formed from bone bioactive glass or ceramic fibers and structural fibers are disclosed. In preferred embodiments, a braid or mesh of interwoven bone bioactive glass or ceramic fibers and structural fibers is impregnated with a polymeric material to provide a composite of suitable biocompatibility and structural integrity. Most preferably, the mesh or braid is designed so that the bioactive fibers are concentrated at the surface of the implant to create a surface comprised of at least 30% bioactive material, thereby providing enhanced bone ingrowth. The interweaving between the bone bioactive glass or ceramic fibers and the core of structural fibers overcomes the problems found in prior composite systems where the bioactive material delaminates from the polymer. Preferred bioactive materials include calcium phosphate ceramics and preferred structural fibers include carbon fibers. Further preferred bioactive materials include aluminum oxide at greater than 0.2%, by mole. Improved prosthetic implants and methods of affixing an implant are thus also disclosed.

8 Claims, 9 Drawing Sheets
(5 of 11 Drawing(s) in Color)

OTHER PUBLICATIONS

F.K. Ko, "Preform Fiber Architecture for Ceramic Matrix Composites," *Bull. Am. Cer. Soc.* (Feb. 1989).

Kokubo et al., "Chemical reaction of bioactive glass and glass-ceramics with a simulated body fluid", J. Materials Science: Materials in Medicine 3, 79–83 (1992).

Kokubo, K., et al. "Apatite Formation on Ceramics, Metals and Polymers Induced by a CaO $SiO_2$ Based Glass in a Simulated Body Fluid", *Bioceramics*, 4, 114–120 (1991).

G. Maistrelli, et al., "Hydroxyapatite Coating on Carbon Composite Hip Implants in Dogs," *J. Bone Jt. Surg.*, 74–B:452–456 (1992).

U. Pazzaglia, et al., "Study of the Osteoconductive Properties of Bioactive Glass Fibers," *J. Biomed. Mater. Res.* 23, 1289–1297 (1989).

Spector, et al., "Porous Polymers for Biological Fixation," *Clin. Ortho. Rel. Res.* 235, 207–218 (1988).

H. Tagai, et al., "Preparation of Apatite Glass Fiber for Application as Biomaterials," *Ceramics in Surgery*, Vincenzini, P. (Ed.), Amsterdam, Elsevier Sci. Pub. Co. (1983), p. 387.

Van Hove et al., *Bioceramics*, vol. 6, P. Ducheyne and D. Christiansen, eds., pp. 319–325, Butterworth–Heinemann, Oxford (1993).

M. Zimmerman, et al., "The Attachment of Hydroxyapatite Coated Polysulfone to Bone," *J. Appl. Biomat.* 1, 295–305 (1990).

COMPOSITE MATERIALS USING BONE BIOACTIVE GLASS AND CERAMIC FIBERS

This is a division of U.S. application Ser. No. 08/436,585, filed May 8, 1995, pending, which is a continuation-in-part of U.S application Ser. No. 08/152,962, filed Nov. 15, 1993 issued as U.S. Pat. No. 5,468,544, Nov. 21, 1995.

The present invention relates to composites made from fibers comprised of bioactive glass and the use of such composites to form implantable surfaces. In particular, the present invention relates to composites comprised of bone bioactive glass or ceramic fibers intermingled with structural fibers such as carbon fibers in a matrix of a polymeric material.

BACKGROUND OF THE INVENTION

Low modulus composite materials have been employed as femoral components of hip implants to reduce stress shielding of the bone and consequently reduce bone tissue resorption. Currently, composite implants are stabilized in their bony bed by a press fit. With this method of stabilization, however, optimum stress distribution effects are not fully realized.

Several attempts have been made to improve the fixation of composite femoral implants to bone. These include porous polymer coatings and particulate bioactive coatings. Implants using porous polymer coatings seek to achieve fixation through mechanical interlocking between the implant and surrounding bone tissue, while the bioactive coatings are designed to attain fixation through a chemical bond between the implant and bone.

Implant surfaces coated with polysulfone particles in an effort to create a porous coating which would behave similarly to a porous metal coating are disclosed in M. Spector, et al., "Porous Polymers for Biological Fixation," *Clin. Ortho. Rel. Res.*, 235:207–218 (1988). Although it is disclosed that some bone growth was evident, the majority of the tissue about the implant surface was fibrous. The porous polymer did not enhance the bone tissue growth in any way.

Composite system of calcium phosphate ceramic powder pressed onto a polymer surface and then cured are also known. See P. Boone, et al., "Bone Attachment of HA Coated Polymers," *J. Biomed. Mater. Res.* 23, No. A2:183–199 (1989); and M. Zimmerman, et al., "The Attachment of Hydroxyapatite Coated Polysulfone to Bone," *J. Appl. Biomat.*, 1:295–305 (1990). These systems are provided in two fashions. First, the ceramic is flush with the polymer surface, hence, only bonding occurs. Second, the calcium phosphate particles extend from the polymer surface. When interfacial bonding is tested, the failure is between the polymer and the calcium phosphate particles. Hence, the interface between the calcium phosphate particles and the polymer is the weak link in the system. These references disclose the use of polyurethane thermoset and polysulfone thermoplastic polymers, a number of other polymers are similarly used as a matrix for a filler of calcium phosphate ceramic powder in U.S. Pat. No. 4,202,055——Reiner et al. The ceramic particles at the surface of this implant resorb and are replaced by bone tissue. There are no structural fibers and the polymer alone is intended to bear the load. This limits the load-bearing applications of this material to those of the polymer. An implantable bone fixation device comprised of an absorbable polymer and a calcium phosphate ceramic powder filler material is disclosed in U.S. Pat. No. 4,781,183——Casey et al. The device disclosed is a temporary load bearing device which resorbs upon implantation. The calcium phosphate particles are added for strength and also resorb, therefore this device is not fixed to bone tissue through the chemical bonding of bioactive material or porous ingrowth.

Structural fibers will improve certain mechanical properties of composite materials. For example, U.S. Pat. No. 4,239,113——Gross et al. discloses a composition of methylmethacrylate polymers and a bioactive ceramic powder combined with vitreous mineral fibers less than 20 millimeters long. This device is used as a grouting material to bond implants to bone tissue. The chopped fibers are not specifically tailored or designed for mechanical property optimization. A similar composition is disclosed in U.S. Pat. No. 4,131,597——Bluethgen et al., which mentions the use of glass or carbon fibers to add strength to the composite. This patent, however, does not specifically discuss placing fibers to achieve bone bonding regionally. Also, no method of optimization of material properties through arrangement of the structural fibers is suggested. Finally, the method of fixation to be achieved by the disclosed material is not explained.

A similar approach using a textured device of carbon fiber/triazin, coated or non-coated with calcium phosphate particles is discussed in G. Maistrelli, et al., "Hydroxyapatite Coating on Carbon Composite Hip Implants in Dogs," *J. Bone Jt. Surg.*, 74-B:452–456 (1992). The results reported show a higher degree of bone contact for the coated devices after six months. However, longer studies are needed to evaluate the long term fatigue effects on the triazin/calcium phosphate interface.

In all these prior art systems, however, it has been found that although a bond between the substrate polymer and bone may be achieved through the use of a bioactive material at the interface, the resulting implant is still unsatisfactory. As discussed above, the significant limitation remains the interfacial bond between the bioactive material and the polymer.

Much of the prior art discussed immediately above utilized calcium phosphate ceramic powders as the bioactive component of the composite. Bioactive glass materials were developed by Hench in 1969. See L. Hench, et al., "Bonding Mechanisms at the Interface of Ceramic Prosthetic Materials," *J. Biomed. Mater. Res.*, 2:117–141 (1971). More recently, elongated, continuous bioactive glass fibers have been fabricated. See U. Pazzaglia, et al., "Study of the Osteoconductive Properties of Bioactive Glass Fibers," *J. Biomed. Mater. Res.*, 23:1289–1297 (1989); and H. Tagai, et al., "Preparation of Apatite Glass Fiber for Application as Biomaterials," *Ceramics in Surgery*, Vincenzini, P. (Ed.), Amsterdam, Elsevier Sci. Pub. Co. (1983), p. 387–393. The latter reference discloses bioactive glass fibers in resorbable bone plates.

As seen from the foregoing, it would be desirable to provide a composite material for use as a prosthetic device that could be designed to provide a structural modulus that closely matched bone. It is thus an object of the present invention to provide composite structures that incorporate a bioactive material in a polymer matrix along with a structural fiber to provide adequate strength. Additionally, it is a further object of the present invention to provide three dimensional and hybrid composite materials that overcome the deficiencies of the prior art, and in particular that provide an adequate interfacial bond between the bioactive material and the polymer.

SUMMARY OF THE INVENTION

It has now been found that bone bioactive glass or ceramic fibers are useful as a chemical bonding vehicle in combination with a structural three-dimensional braided fiber substrate. The bioactive fibers enhance bone growth and bond to surrounding bone tissue. These bone bioactive glass or ceramic fibers are interwoven in the three dimensional braid with carbon fibers and infiltrated with a thermoplastic polymer to form a three-dimensional bioactive composite material. The glass fibers are preferably concentrated on the outer surface of the composite so as to be exposed to physiological fluids upon implantation. This leaves the carbon fibers concentrated in the center region of the implant material to bear the majority of the load.

The stress transfer achieved by interfacial bonding between the implant and bone, combined with the "matched modulus" of the composite implant, provides near optimal stress distribution in the bone, thereby improving long term stability and fixation. In addition, with adequate fixation, there is decreased micromotion between the implant and bone, hence the potential for abrasion of the composite material surface is greatly reduced. Consequently, the chances of particulate debris from the implant causing an inflammatory response, which often leads to loss of implant stability, are also greatly reduced.

BRIEF DESCRIPTION OF THE DRAWINGS

The file of this patent contains drawings executed in color. Copies of this patent with color drawings will be provided by the Patent and Trademark Office upon request and payment of the necessary fee.

DETAILED DESCRIPTION OF THE PREFERRED EMBODIMENTS

Figure 1:
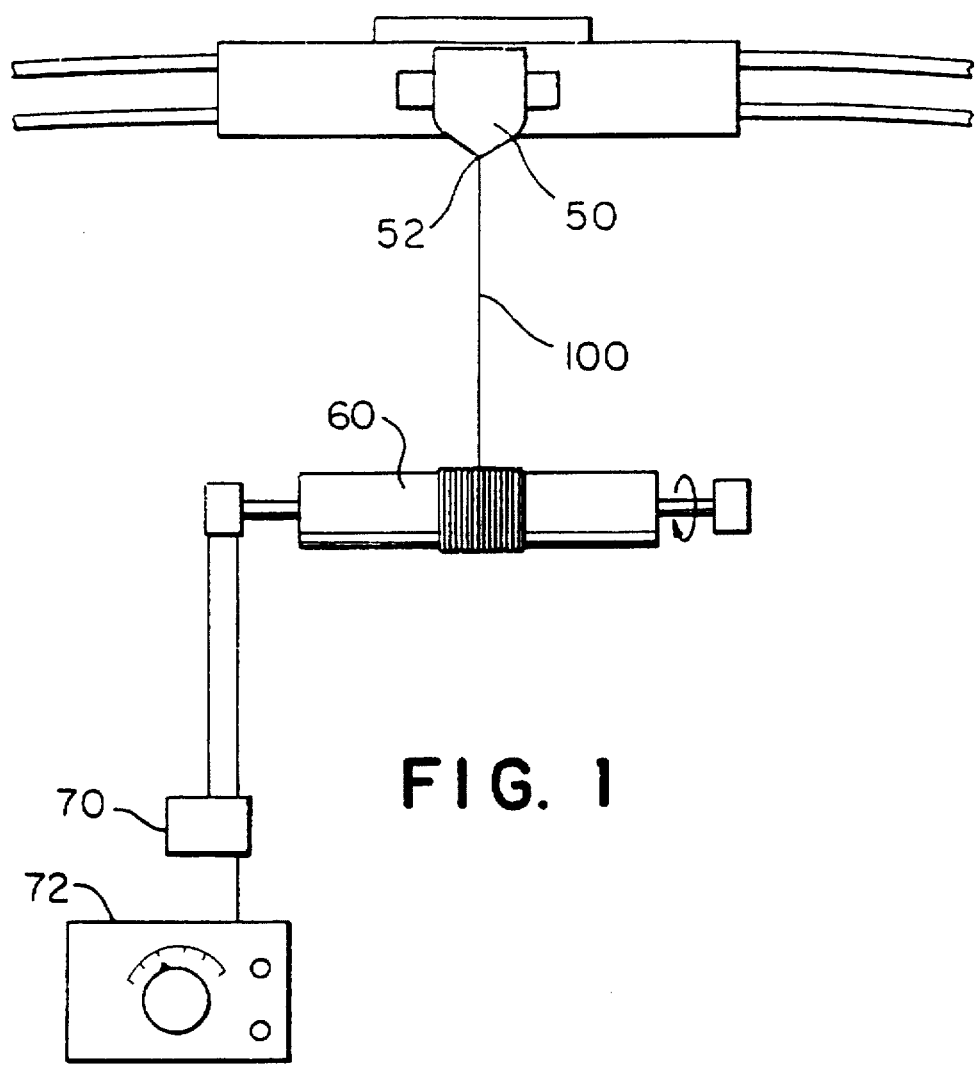
FIG. 1 is an illustration of the apparatus used to draw bone bioactive glass or ceramic fibers used in the present invention.

The uniquely constructed composite material of the present invention is able to maintain continuity from the interface of the structural substrate and the carbon fiber/polymer interface, and to the interface between the bioactive surface and the bioactive glass fiber/polymer interface. As explained below, the bioactive section of the implant material is integrally incorporated into the substrate through a braided interface. Because of this construction there is an increased bond surface between the bioactive material and the polymer that imparts a higher degree of integrity to the bioactive composite material as compared to a particulate coating on the surface of a polymeric composite, such as that found in the prior art. Thus, the likelihood of delamination of the bioactive material from the polymer is greatly reduced. Thus, the present invention provides interfacial bonding between the polymer and bioactive coating, overcoming the main limitation of the prior art.

The configuration of the fiber architecture results in the load being applied to a central portion of the composite, which is preferably comprised of strong, inert fibers such as carbon fibers or other biocompatible fibers integrated with the bioactive fiber surface. Stress is therefore transferred from the inert structural fibers to the bioactive fibers at the implant surface. The integration also serves to increase the mechanical integrity of the material system and prevent delamination within the composite structure.

In the local environment of the bioactive glass fiber, a partial degradation occurs. As the bioactive glass fiber is resorbed it is replaced by bone tissue; the bone tissue is chemically bonded to the glass fiber and also interlocked with these fibers. Furthermore, the bioactivity reactions occurring at the glass surface lead to a precipitation layer on the polymer. This layer, in turn, promotes bone tissue formation and bonding. The triple means of interfacial bonding leads to an interface which stabilizes the implant in its bony bed and provides stress transfer from the implant across the bonded interface into bone tissue. The bone is stressed, thus limiting bone tissue resorption due to stress shielding. This significant occurrence will increase the life of an implant because fixation and stability will not be lost due to bone tissue resorption, which is an initiator in the cascade of events leading to prosthesis loosening.

In the present invention, a composition of bone bioactive glass or ceramic fibers is preferred. In the case of glass the preferred composition leads to a slowly reacting glass while maintaining the ability to be fabricated. A slow reaction rate is desired because a large surface area of glass is exposed to physiological solutions during implantation with glass in a fibrous configuration. A bioactive glass that quickly degrades may lead to an adverse inflammatory response, impeding bone growth and bonding. The tradeoff is that since the glass must be drawn into continuous fibers it cannot be too viscous or too fluid, or the fibers would break upon drawing. Describing the compositional range for materials capable of being drawn into bioactive glass or ceramic fibers thus involves bioactivity versus manufacturability. A most preferred composition that can be successfully drawn into fibers while maintaining bioactivity is: 52% $SiO_2$; 30% $Na_2O$; 15% $CaO$; 3% $P_2O_5$. In developing this range, experimental trials showed that a composition of 52% $SiO_2$; 32% $Cao$; 3% $P_2O_5$; 13% $Na_2O$; would be bioactive, however, it is difficult to draw this composition of glass into fibers. This is because the $CaO$ and the $P_2O_5$ work against fiberization, while the $Na_2O$ and $SiO_2$ work for it. It was also found that a composition of 52% $SiO_2$; 27% $CaO$; 2% $P_2O_5$; 19% $Na_2O$ led to the same difficulties relating to fiberization. The following trends were seen among experimental batches:

|  | Fiberization | Bioactivity |
|---|---|---|
| $SiO_2$ | increases | 40–60% give bioactivity, decreased bioactivity with higher $SiO_2$ |
| CaO | decreases | increases |
| $P_2O_5$ | decreases | increases, but not required to achieve bioactivity |
| $Na_2O$ | increases | decreases |

Thus, in preferred embodiments, glass compositions used with the present invention will be comprised of 40–60% $SiO_2$; 10–21% CaO; 0–4% $P_2O_5$; and 19–30% NaO. A more preferred range will be comprised of 45–55% $SiO_2$ 15–20% CaO; 25–35% $Na_2O$; and 0–3% $P_2O_5$ by mole. As noted above, the most preferred composition on the criteria of slow reaction rate and the ability to be manufactured is 52% $SiO_2$; 30% $Na_2O$; 15% CaO; 3% $P_2O_5$ by mole. Modifiers which may be added to the base composition (by mole) include: 0–3% $K_2O$; 0–2% MgO; 0–1% $Al_2O_3$; and 0–3% $F_2$. Preferably, $Al_2O_3$ is added in an amount greater than 0.2%. As known in the art, such modifiers may be added in small quantities to vary the properties and process parameters and further improve the control of bioactivity and manufacturability.

The following Examples will discuss and explain the formation of a continuous fiber of a bioactive glass for use in a braided fiber and a woven fabric, both of which are impregnated with a polymeric material such as polysulfone to create a three dimensional composite material.

EXAMPLE I

The most preferred glass fiber composition disclosed immediately above (52% $SiO_2$, 30% $Na_2O$, 15% CaO, and 3% $P_2O_5$ (in mole %)) was prepared from powders. The powders were weighed, mixed, and melted at 1350° C. for two hours in a silica crucible. The glass drawing apparatus used for this Example is shown in FIG. 1 and includes a resistance heated platinum crucible 50 with an orifice at the bottom. Glass shards were placed into the crucible 50 and melted at approximately 1150° C. The viscous melt formed a meniscus at the crucible orifice 52. To form the fiber 100, the glass meniscus was gently touched with a glass rod and the glass rod was quickly, yet smoothly, pulled from the crucible orifice 52 to form a glass fiber 100 from the melt. The fiber 100 was manually pulled and attached to the take-up wheel 60 spinning at 300–500 rpm, as determined by the speed control 72 attached tot he motor 70 that rotates the take-up wheel 60. A smooth, continuous glass fiber 10–13 microns in diameter was obtained.

Polymer plates were manufactured using a closed die and a hot press. The polymer (polysulfone) was weighed and dried in an oven at 163° C. for two hours to drive out excess moisture. The mold was cleaned with ethanol and sprayed with teflon mold release. The thermoplastic powder was poured into the mold and the mold was placed in the hot press. The press was heated to 260° C. and pressure was then applied to 14,000 lbs and released. This was repeated twice. The mold was then heated to 300° C. and a pressure of 620 psi was maintained for thirty minutes. At this time the pressure was released and the mold was air cooled.

The same processing parameters were followed to make plates of a composite material. The polymer was first mixed with chopped glass fibers and then processed with the closed die in the hot press, as described above.

Plugs 4 mm in diameter and 3 mm thick, were machined out of both the polymer plates and the plates that included the chopped bioactive fibers using a core drill tip. The samples were then cleaned with soap and water to remove cutting fluids, and ultrasonically cleaned in ethanol and deionized water, being dried after each cleaning. The implants were sterilized with ethylene oxide.

One bioactive glass fiber/polysulfone and one control polysulfone plug were implanted bilaterally in the medial proximal aspect of the tibia using aseptic techniques. Each rabbit served as its own control. Five rabbits were euthanized at three weeks and five at six weeks.

The retrieved tibiae were immersed in formalin fixative for two weeks. They were rinsed in deionized water and gross sectioned with a low speed blade saw using 70% ethanol as cutting fluid. The sections were dehydrated according to a graded alcohol immersion plan from 70% ethanol to 100% absolute ethanol over a two week period. Following dehydration, the specimens were sectioned perpendicular to the implant long axis into approximately 1 mm thick sections. The sections were infiltrated with Spurr's embedding media according to a graded infiltration sequence in a vacuum desiccator using polyethylene embedding molds. The Spurr's infiltration cycle was as follows:

| 25% Spurr's*/75% ethanol | 2 days (change day 2) |
|---|---|
| 50% Spurr's*/50% ethanol | 2 days (change day 2) |
| 75% Spurr's*/25% ethanol | 2 days |
| 100% Spurr's* | 1 day |
| 100% Spurr's (.04 DMAE) | 1 day |

*No DMAE (n,n-dimethylaminoethanol) added

The specimens were then cured for 2 days in an oven at 21° C. Following embedding, the specimens were sectioned to approximately 0.5 mm thick sections using a low speed diamond wafered rotating blade saw. These sections were ground and polished using 800 and 1200 grit paper to a final section thickness of about 50 μm. The sections were stained using Villanueva Mineralized bone Stain (Polyscientific, New York).

Figure 2:
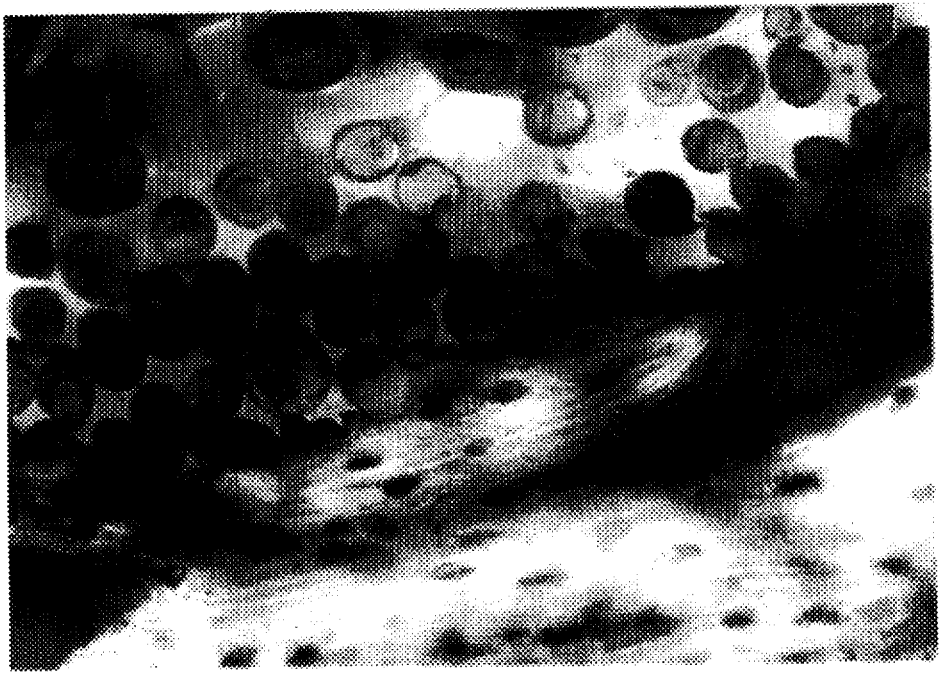
FIG. 2 is a photomicrograph of a section of bone showing ingrowth achieved in an implant.
Figure 3:
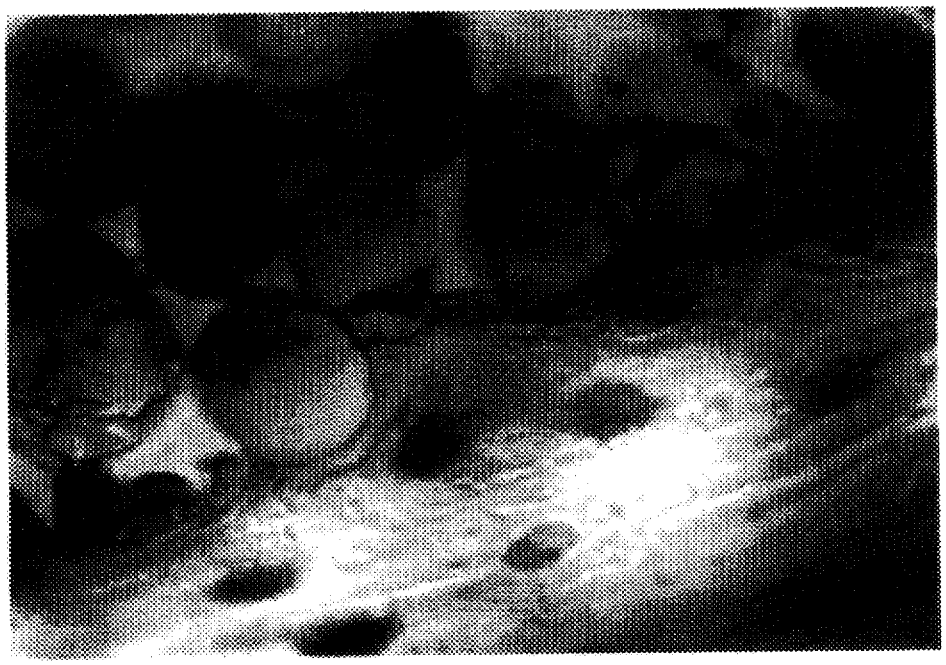
FIG. 3 is a photomicrograph of a section of bone similar to FIG. 2, but taken at higher magnification.

As seen in FIG. 2, taken at 400×. The composite material shows very close apposition to bone in areas of high fiber concentration. In these areas, bone bioactive glass or ceramic fibers are partially resorbed, more clearly seen in FIG. 3, taken at 1000×. In addition, in regions where fibers are close together and bone apposition is achieved, there is also bone apposition to the adjacent polysulfone matrix. In contrast, the polysulfone implants show bone tissue surrounding the plug, but with an interposing layer between the implant and bone tissue.

Thus, the foregoing Example shows that the bioactive glass fiber/polysulfone plugs made in accordance with the present invention achieve a bond between surrounding bone tissue and the glass fibers at the implant surface. The bonded fibers are partially resorbed with bone tissue replacing the glass. Consequently, the method of glass fiber fixation to bone is not only by chemical bonding, but also by micromechanical interlocking. Additionally, there appears to be a bond between the adjacent polymer and surrounding bone tissue. This would lead to increased areas of fixation between the composite and bone beyond that of the fiber itself.

The bond between polysulfone and bone may be due to a calcium phosphate layer being precipitated onto the adjacent polymer surface as it was being precipitated onto the glass fiber. Once this calcium phosphate layer is formed, the polymer itself may act as a substrate for bone growth.

Similar findings after implantation of a titanium fiber/bioactive glass composite in dogs were recently reported. Van Hove et al., *Bioceramics Vol. 6*, P. Ducheyne and D. Christiansen, eds., pp. 319–325, Butterworth-Heinemann, Oxford (1993). This study shows bone growth over a titanium fiber which was between two islands of bioactive glass. If the separation between the glass was less than 50 microns, the titanium was covered with bone, but if it was greater than 100 microns (two fiber diameters) there was incomplete bone coverage. An in vitro study has concluded that when a polymer is faced 1 mm or less away from a bioactive glass in simulated body fluid, a calcium phosphate layer is precipitated onto the polymer surface. See T. Kokubo, et al., "International Symposium on Ceramics in Medicine," Butterworth-Heinemann Ltd., London (1991).

The histological observations of the foregoing Example indicate that bone bioactive glass or ceramic fibers in combination with polysulfone polymer will bond to bone tissue. This finding indicates that bone bioactive glass or ceramic fibers on the surface region of low modulus composite implants, such as hip stems and bone plates will achieve improved results.

Another aspect of the present invention is the optimization of the amount of fiber used in the composite. As explained above, previous bioactive polymeric composites had used continuous particle coatings on the surface of polymers or polymeric composites with a bioactive powder dispersed through the polymer matrix. It has been determined having surface area partially covered by bioactive glass in a composite form leads to bone bonding in vivo. A calcium phosphate layer is the substrate for bone growth. As explained above, the desirable development of a calcium phosphate layer on a non-bioactive material is possible if the material is in close apposition to the bioactive glass. Consequently, it has been found that a composite with only a partial bioactive surface would still achieve bonding. Preferably, the proportion of bioactive surface area exposed should be greater than 30% of the total surface area and the bioactive material should be homogeneously distributed over the surface of the composite to maintain the 30% surface area of bioactive material over the entire surface desired for fixation.

Based upon the foregoing, it has also been discovered that fibers made in accordance with Example I and similar fibers can be advantageously used in composite materials that incorporate a structural fiber along with the polymer and the bioactive fiber. Thus, the present invention also relates to composite materials formed of woven, intermingled or juxtaposed elongated fibers of both a bioactive material and another material chosen for its structural properties. These two fibers are combined in a polymeric matrix. The following Examples will illustrate embodiments of this aspect of the present invention.

EXAMPLE II

Figure 4:
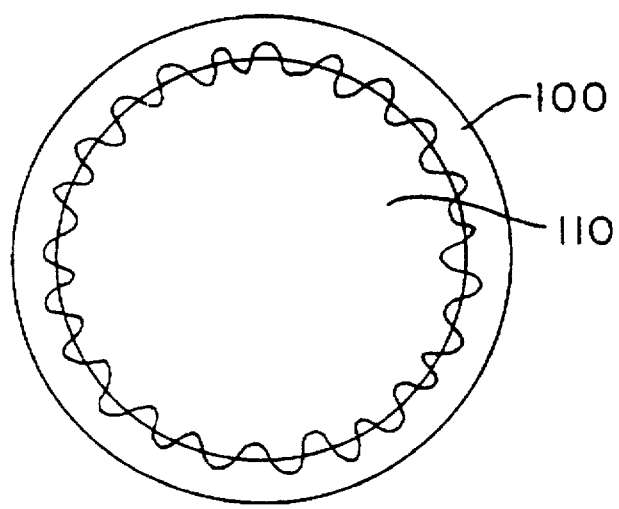
FIG. 4 is a cross-section of a composite fiber braid made in accordance with the present invention.

One manner by which the location and density of fibers within a composite can be controlled is by forming a braid of one or more types of fibers and impregnating the braid with a filler material, such as a polymer. In preferred embodiments of the present invention, continuous bone bioactive glass or ceramic fibers are grouped into 5000 filament fiber bundles. The fiber bundles (or "tow") are interwoven with carbon fibers into a braided textile preform. Most preferably, the bone bioactive glass or ceramic fibers are made in accordance with the composition formulation set forth above. As seen in FIG. 4, a preferred construction has glass fibers 100 woven into a three dimensional tube about a central, but separate, carbon fiber core 110. The two braids are woven simultaneously while the carbon fibers in the core 110 and glass fibers 100 at the carbon/glass interface are interwoven, overlaid or otherwise intermingled. This results in structural interlocking and brings continuity to the structure, even before the polymer is infiltrated.

To create a composite in accordance with this embodiment of the invention, the carbon fibers in the core 110 are commingled with polymer and unidirectional thick polymer fibers are intermingled with the glass fibers 100 in the outer region of the preform. The hybrid preform is then processed in a closed die using a hot press, as described above. The amount of polymer is calculated to give the final total volume fraction desired, thus no additional polymer is added before processing. Also, the resulting composite does not need to be injection molded due to the placement of the polymer fibers so as to achieve uniform polymer distribution throughout the fibrous preform. The final composite is machined to expose bioactive glass 100 fibers at the surface.

The present invention is also directed to the integration of a bioactive phase in fibrous form into a carbon fiber, three dimensional structural reinforcement network. This results in a delamination resistant, interpenetrating fibrous network which allows bone tissue ingrowth.

EXAMPLE III

To facilitate composite processing, a thermoplastic matrix in filamentous form is co-mingled with the reinforcement fibers. As a result, the thermoplastic fibers are uniformly distributed through out the structure. A composite can be formed with bioactive fibers and by the application of heat and pressure to melt the thermoplastic according to well-established regimens known in the art.

By proper selection of fiber architecture and textile processing technique, the quantity and distribution of the bioactive phase can be controlled so that a preferred concentration of the bioactive fibers it disposed near the surface of the structure. The thermal and mechanical properties of the composite system can be further tailored by changing the fiber volume fraction and fiber orientation distribution. Depending on the type of implant, two or three dimensional fiber architectures can be selected and fabricated into net shape or near-net shape fibrous assemblies by weaving, knitting or braiding techniques, such as those disclosed in F. K. Ko, "Preform Fiber Architecture for Ceramic Matrix Composites," *Bull. Am. Cer. Soc.* (February 1989).

For illustrational purposes, a three dimensional hybrid mesh will be provided as a specific example. It should be noted, however, that the same principles can be applied to cylindrical shapes and other complex structural shapes as seen in the three dimensional braiding loom design diagram illustrated in FIG. 5.

Figure 5:
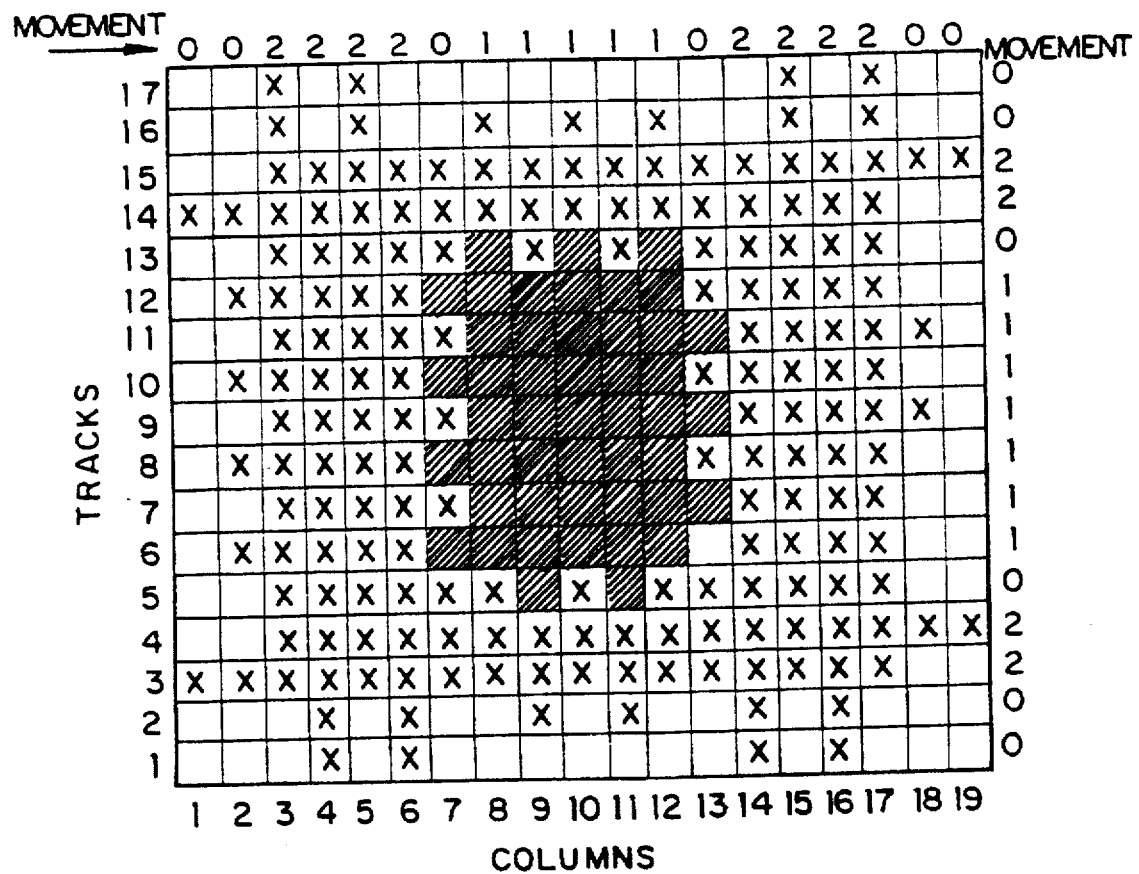
FIG. 5 is a schematic illustrating the orientation and placement of fibers in a textile woven from bone bioactive glass or ceramic fibers and structural fibers in accordance with the present invention.

In FIG. 5, the X's represent the bone bioactive glass or ceramic fibers, the number and distribution of which can vary, and the O's are a structural fiber, preferably carbon fibers, which also may be provided in large and small bundles. The vertical rows of the loom are called "tracks" whereas the horizontal rows of the loom are "columns." As known in the art, a three dimensional braided structure is fabricated on the alternate motions of tracks and columns of bundles of fibers attached to a carrier based on the movement instructions indicated in the track and column direction in an alternate manner. An "0" means no movement, and a "1" means moving in the positive direction by one carrier position and a "−1" means moving the carrier in the opposite direction of the other half of the carrier in the same direction. Naturally, a "2" means moving two carrier positions.

In a preferred embodiment, the integration of the bone bioactive glass or ceramic fibers into the carbon fiber in an interfacial region is accommodate by the position of the carrier in track/column coordinates 6/6, 6/7; 7/7, 7/8; 8/6, 8/7; 9/7, 9/8; 10/6, 10/7; 11/7, 11/8; 12/6, 12/7; 13/7, 13/8 being exchanged after each cycle of track/column movement.

From the foregoing, it can be seen that for a given yarn bundle size, the fiber orientation and fiber volume fraction can be designed. Knowing the fiber and matrix material properties, the elastic properties in the form of a stiffness matrix can be established for the composite. Finite element analysis can also be performed to assess the stress-strain response of the implant under a set of boundary conditions. This preform design, micromechanics analysis and structural mechanics analysis can be performed in an iterative manner to optimize the design of the implant and predict the performance capability of the structure.

Figure 6:
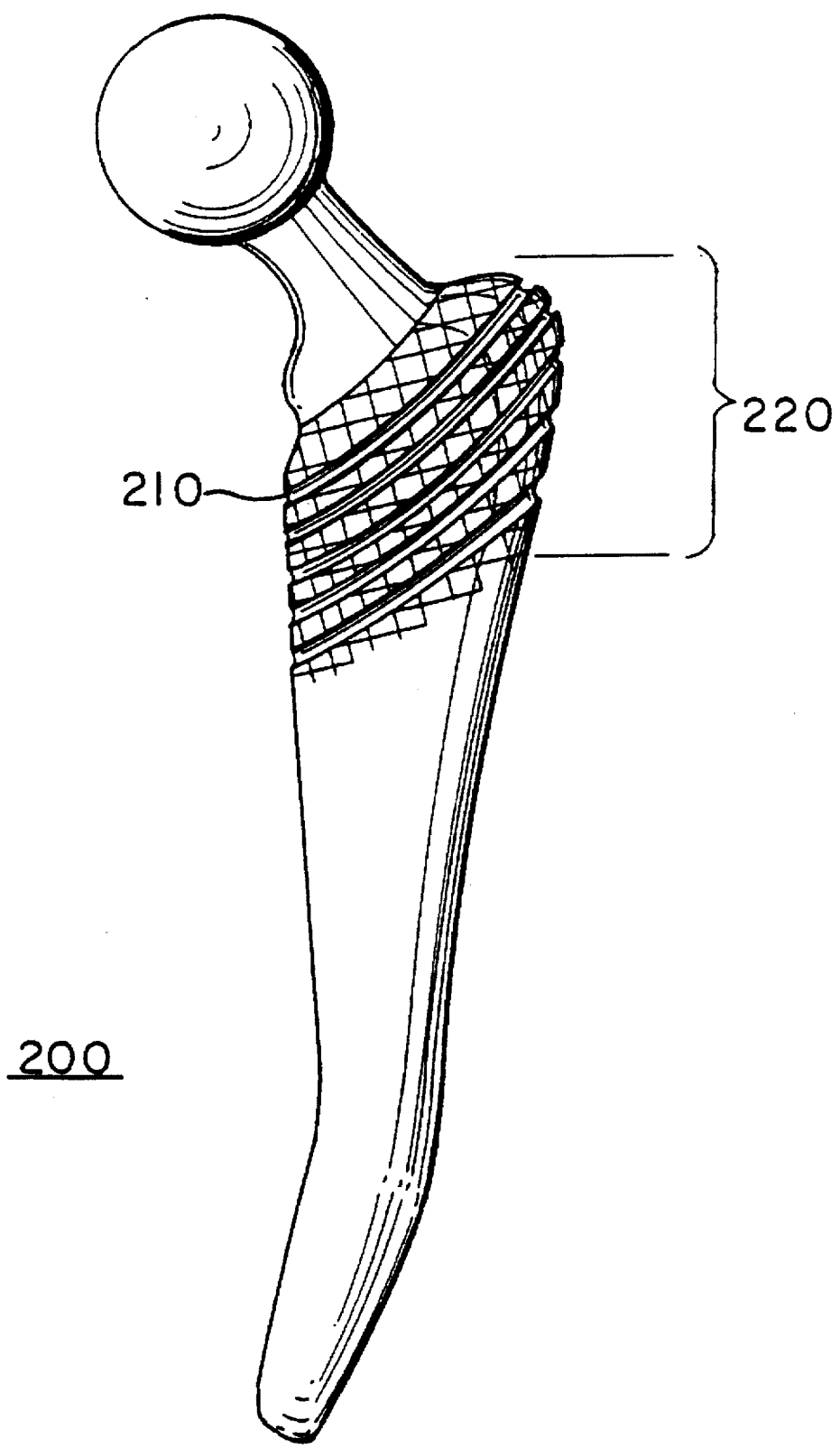
FIG. 6 an elevation view of a hip prosthesis made in accordance with the present invention.

Additional aspects of the present invention will best be understood with reference to FIG. 6, which illustrates a hip implant prosthesis 200 as an example of a composite structure that can be constructed using the present invention. First, it will be understood by those of skill in the art that the surface, or part of the surface of the prosthesis 200 can be covered with grooves 210 or other surface irregularities. For example, as seen in FIG. 6, it is preferred that the proximal circumferential third of the prosthesis 220 have grooves. These features aid in the macroscopic aspects of bone fixation and have been shown to be beneficial. In accordance with the present invention, the grooves 210 are most preferably formed by molding the preform to the desired texture, rather than machining a smooth surface.

Additionally, the present invention also permits bioactive and structural fibers to be localized to achieve a local fixation using a bioactive surface. In other words, the fibers can be varied so that the bioactivity is concentrated at a particular section or portion of an implant, device or prosthesis. Referring still to FIG. 6, the hip prosthesis 200 would most preferably have the bioactive fibers concentrated in the proximal one third 220 of the implant device. It has been shown that proximal stress transfer in a total hip arthroplasty is better achieved by using a material with fixation to bone in this region.

Thus, it will be appreciated that the present invention is very versatile in many of its parameters. The bone bioactive glass or ceramic fiber can be selected from bioactive glass or glass-ceramic materials, including calcium phosphate ceramic fibers. The polymer system used may be any polymer which bonds to the bone bioactive glass or ceramic fibers, is biocompatible, and does not inhibit the bioactivity of the fibers in vivo. Examples of such polymer systems are polysulfone, polyetheretherketone (PEEK), and polyetherketoneketone (PEKK). The structural fiber can be any inert fiber that fits the constraints of biocompatibility and exhibits the ability to bond to the chosen polymer. In addition to the carbon fibers disclosed above, such fibers include inert high strength glass, aramid fibers, and inert ceramic fibers, such as alumina. The fiber orientation and type of weave may be varied for different applications and can be pre-selected and optimized using well known analysis techniques. Moreover, the disclosed hybrid woven bioactive composite can be constructed not only as the three dimensional braided textile structure discussed above, but any woven textile structure such as a two-dimensional braid, fiber interlock weave, or laminated composite, among others. Finally, those of skill in the art will understand that the present invention may be adapted to many applications where material shape, strength, stiffness, and fixation to bone are among the design parameters. In accordance with the present invention fibrous composites of biocompatible materials can be made into bioactive composites by incorporating bone bioactive glass or ceramic fibers into the weave at the bone contact surface.

EXAMPLE IV

Glass fibers having a molar composition of 52% $SiO_2$, 15% CaO, 3% $P_2O_5$, and 30% $Na_2O$ were supplied by Glass Incorporated International, Covina, Calif., USA. The glass fibers were weighed and immersed in a simulated blood plasma solution (SBF) which consisted of trishydroxymethylaminomethane complimented with the following ions: 152 mM $Na^+$, 135 mM $Cl^{2+}$, 5 mM $K^+$, 2.5 mM $Ca^{+2}$, 1.5 mM $Mg^{+2}$, 27 mM $HCO_3^-$, 0.5 mM $SO_4^-$, and 1.0 mM $H_2PO_4^-$, at the following time periods: 1, 3, and 8 hours and 1, 3, and 10 days. Using an average glass fiber diameter of 15 microns, the fiber surface area to solution volume ratio was selected as 0.08 $cm^{-1}$, which led to a post immersion pH in the physiological range.

The samples were immersed in closed vials on a shaker table moving at 200 rev/min in an incubator at 37° C. Upon removal from solution the fibers were rinsed in acetone and dried in an oven at 37° C.

The reacted fibers were characterized using scanning electron microscopy with energy-dispersive X-ray analysis (SEM/EDXA). For SEM/EDXA, the fibers were mounted on an aluminum stub with silver paint and ion sputter coated with carbon to enhance conductivity. The analysis was performed at 15kV on a Joel JSM-T330A scanning microscope, Peabody, Mass., USA, with a KEVEX surface analysis system, Fisons Instruments, San Carlos, Calif.

The SEM and EDXA results were obtained for the surface of unimmersed glass fibers and the six immersion times: 1, 3, and 8 hours, 1, 3, and 10 days. In the first three hours of immersion in SBF there was a decrease in the sodium peak, while the glass fiber surface showed limited change in morphology.

A reduction in sodium on the surface of the glass was identified in the first eight hours, using EDXA. After one day of immersion in SBF, the calcium and phosphorous peaks were greatly reduced and the silicon peak showed high intensity, as determined by EDXA. Uniformly dispersed snowflake-like formations were dispersed over the surface of the fibers. These regions measured approximately 5 microns in diameter and appeared flat against the surface of the glass fiber. The snowflake-like formations had strong silicon peaks, but also showed the presence of calcium and phosphorous, as well as smaller amounts of sodium and chlorine.

After three days of immersion in SBF, per EDXA, the silicon peak was much less intense, while the calcium and phosphorous peaks were strong. Here the ratio of calcium to phosphorous was 1.2. The surface of the glass fiber had non-homogeneously dispersed nodules which ranged from 1–4 microns in diameter. The larger nodules seemed to be a combination of smaller ones which had agglomerated. These nodules were not flush with the fiber surface. The underlying areas of the fiber, without large nodules showed a more mottled surface which was fairly homogeneous.

After a ten day immersion period, the silicon peak was absent from the surface scan, which indicated the presence of only calcium and phosphorous, as determined by EDXA. The calcium to phosphorous ratio was 1.4. The morphology of the fiber surface was much like that after three days immersion, although even larger nodules and a more textured surface was present. The nodules had grown to approximately 5 microns in diameter.

Figure 7:
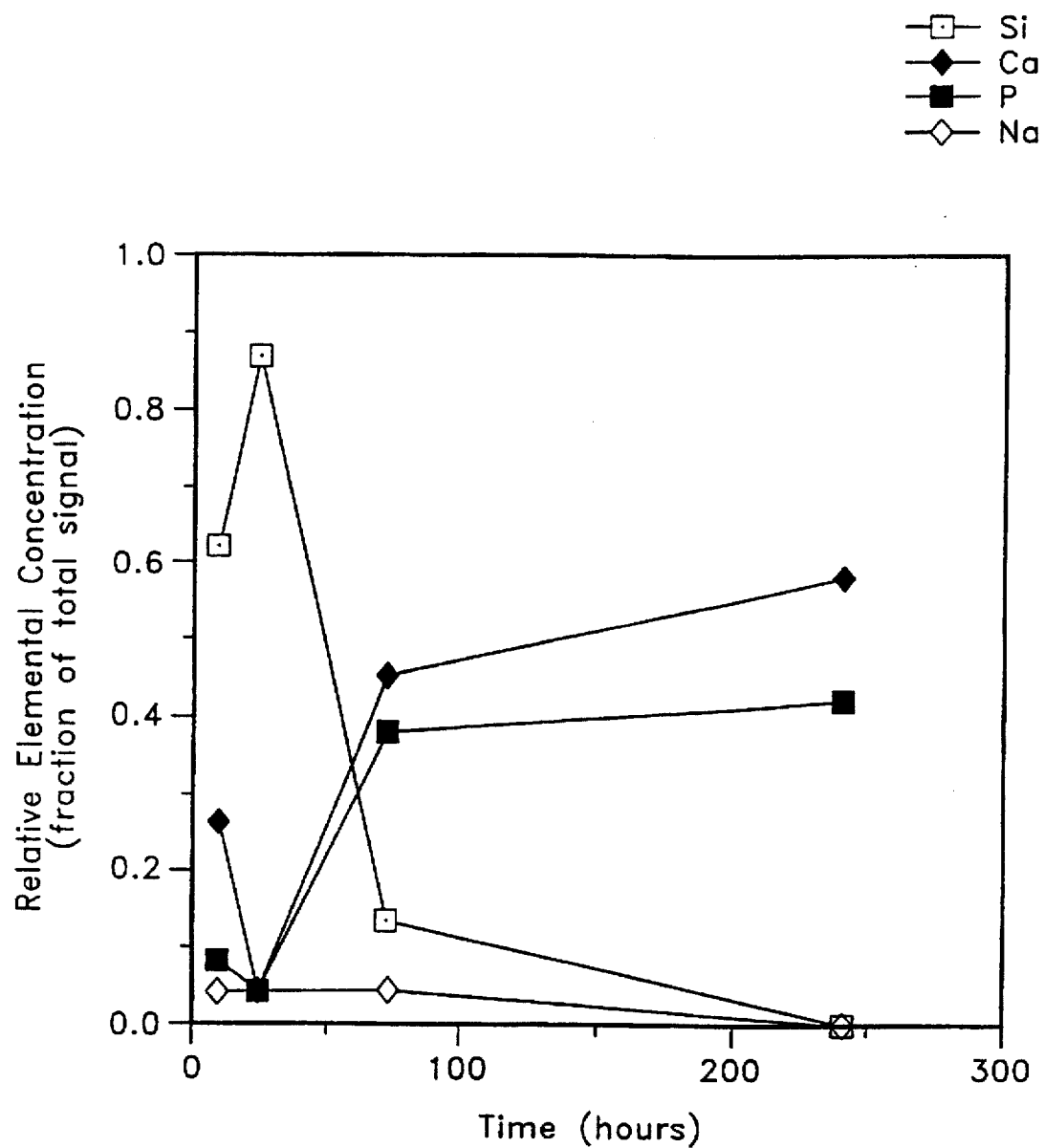
FIG. 7 depicts the elemental concentration on the glass fiber surface after immersion in simulated body fluid versus time.

The elemental concentrations of silica, calcium, phosphorous, and sodium, as measured by EDXA, versus immersion time are depicted graphically in FIG. 7.

Classification of the in vitro reaction stages of the bioactive glass fibers according to the Hench system puts stages 1–3 in the first eight hours to 1 day. Stage 4 corresponds to 3 days immersion and Stage 5 is at 10 days immersion. A significant difference between 45S5 bioactive glass results and our own glass fibers is in the time differential. By 8 hours immersion, 45S5 bioactive glass had completed Stage 4 and was beginning Stage 5, which plateaus out to eleven days. In the bioactive glass fibers, Stage 5 or the formation of crystalline calcium phosphate did not occur at 3 days but was present at 10 days. Therefore, the bioactive glass fibers exhibited a reduced rate of surface reactivity, when compared to 45S5 bioactive glass.

While a slower rate of reactivity could be explained by crystallinity in the glass, our glass fibers were determined to be amorphous. A more likely explanation of the reduced rate of reactivity is related to the glass composition. $Al_2O_3$ was shown to be present in the glass by X-ray fluorescence and chemical analysis in a quantity greater than previously incorporated, and less than 1% by weight.

The Covina fibers were analyzed using X-ray fluorescence to identify any contaminants within the glass fibers. The chemical composition of the Covina fibers was verified using standard glass chemical analysis techniques. For chemical analysis, the glass was attacked with a mixture of hydrofluoric and perchloric acids. After evaporation, the residue was dissolved with nitric acid and diluted to 250 mL. The elements were analyzed by atomic absorption spectroscopy, colorimetry and gravimetry. These analyses were performed by Institut National du Verre, Charleroi, Belgium.

X-ray diffraction (XRD) measurements using the Covina fibers were taken as 2θ varied from 10–150 using an automatic Rigaku diffractometer with Cu Kα. Data collection was performed with a receiving slit of 0.15 mm, a 2 scanspeed of 1/min and a 2 scanstep of 0.02. Only non-immersed fibers were evaluated to determine the degree of crystallinity of the glass fibers.

XRD showed a low broad peak representing an amorphous material and several sharper peaks. The sharper peaks corresponded to those of aluminum which came from the sample holder. The as-drawn fibers were therefore amorphous. Because the gel layer is the weakest portion of the bond, a reduction of the silica layer thickness would seem to result in increased interfacial bond strength.

X-ray fluorescence was used to determine the relative amounts of compounds present in the glass fibers. The results are presented in Table I. Precise compositional concentrations could not be obtained using this method for our glass because no prior standards have been developed for this unique glass composition. The main elements were found in the proportions shown, as were smaller quantities of other elements, including modifiers. Most modifiers were determined to be present in amounts previously used in the art. Surprisingly, however, the modifier $Al_2O_3$ was determined to be present in an amount greater than previously used ——0.95%.

TABLE I

| Oxide | Weight % |
|---|---|
| SiO2 | 53% |
| Al2O3 | 0.95% |
| Na2O | 28.9% |
| K2O | 0.05% |
| CaO | 15.8% |
| MgO | 1.42% |
| Fe2O3 | 0.10% |
| TiO2 | 0.05% |
| P2O5 | 5.9% |
| SO3, ZrO2 | trace |

Chemical analysis using atomic absorption spectroscopy, colorimetry, and gravimetry are more quantitative in the absence of a previously developed standard than X-ray fluorescence. The results for this chemical analysis are shown in Table II in weight percentages. Again, $Al_2O_3$ was found to be present at an amount greater than previously used ——0.65%.

TABLE II

| Oxide | Weight % |
|---|---|
| $SiO_2$ | 50.63 |
| $Al_2O_3$ | 0.653 |
| $Na_2O$ | 26.80 |
| $K_2O$ | 0.020 |
| CaO | 13.90 |
| MgO | 1.379 |
| $Fe_2O_3$ | 0.062 |
| $TiO_2$ | 0.008 |
| $P_2O_5$ | 6.30 |
| $SO_3$ | 0.041 |
| $ZrO_2$ | 0.013 |

The addition of the multivalent cation ($Al^{+3}$) to the glass composition has been previously shown to greatly reduce the rate of bioactivity (Gross et al., *CRC Critical Reviews in Biocompatibility*, 4:2 (1988); Hench, L. L., *Handbook of Bioactive Ceramics*, Vol. I, T. Yamamuro, L. L. Hench, and J. Wilson, eds., pp. 7–23, CRC Press, Boca Raton (1990); Kokubo et al., *High Tech Ceramics*, P. Vincenzini, ed., pp. 175–184, Elsevier, B. V., Amsterdam (1987); Kokubo et al., *Materials in Medicine*, 3:79–83 (1992); and Kokubo et al., *Proceedings of XV International Congress of Glass*, Vol. 3a, O. V. Mazurin, ed., pp. 114–119, Leningrad (1988)) primarily due to the increased network forming of the oxide. It has been hypothesized that alumina can tie up hydrated silica gel which results in limited or inhibited calcium and phosphorous formation within the gel layer (Gross et al., 1988, supra). Further, $Al^{+3}$ ions may precipitate onto the surface and form carbonates, oxides, or hydroxides (Hench, L. L., 1990, supra), also preventing the incorporation of calcium and phosphorous in the gel.

The foregoing results indicate that the greater $Al_2O_3$ content has, surprisingly, counteracted the effect of $Na_2O$ on rate of surface reactivity in the present fiber composition. As is disclosed below, this improved performance of the fibers in vivo.

EXAMPLE V

Composites as described in Example IV and all-polymer control specimens were implanted in the femoral cortex of eighteen rabbits. Eight rabbits were euthanized at three weeks and ten at six weeks. The retrieved sections of implant and bone were evaluated mechanically to quantify the interfacial bond strength; histologically, to observe the bone tissue/biomaterial interactions; and histomorphometrically, to quantify the amount of bone tissue present at the implant surface.

Both the polymer and the composite plates were fabricated using the same methods as described above. The composites contained approximately 30% by volume of glass fibers. The plates were machined into 3mm (0.125 in.) diameter and 15 mm (0.6 in) length implants. The surface roughness of the implants was determined using an optical profiler (Wyco, Tuscon, Ariz.).

One composite and one control polysulfone specimen were implanted bilaterally in the distal femur using aseptic techniques. The animals were anesthetized, shaved and prepped with betadine solution. The skin was incised, muscle layers were separated, and the periosteum was elevated away from the bone surface. A scalpel was used to mark the location of the implantation site and then a hand-powered drill with burr was used to create the transcortical cylindrical defect into which the plug was press-fit. Closure was in two stages: continuous sutures closure of the periosteum and soft tissue and continuous subcutaneous closure of the skin. The wounds were dressed and antibiotics were administered three days post-operatively. Radiographs were taken within one week after surgery. Eight rabbits were euthanized at three weeks and ten at six weeks.

After euthanasia by injection of nembutal, each femur was harvested. The bones were gross sectioned in the region of the implant using saline as a cutting fluid while maintaining moisture in the samples. The implant/bone composite was then sectioned transverse to the long axis of the implant, leaving half of the implant/bone section for mechanical test and the remaining half for histology. The mechanical test specimen was then stabilized in the test fixture using an acrylic polymer with the long axis of the implant perpendicular to the flat bottom of the fixture. Still keeping the sample moist, the assembly was placed in a manner to align the specimen long axis with the load direction.

Testing was performed on an Instron mechanical test machine (Model 1321) using a cross-head speed of 5 mm/min (0.2 in/min). Load and cross-head displacement data were recorded on a personal computer using Labtech Notebook (Laboratory Technologies Corporation) software at a sampling rate of 10 measurements/sec.

Of the thirty-six femora which were implanted with either a composite or polymer biomaterial, thirty-four were mechanically tested. A three week femur was fractured and the implant was removed from the mechanical test experiment; a six week polymer implant was not included in the data because the implantation site was too close to the femoral condyles.

Figure 8:
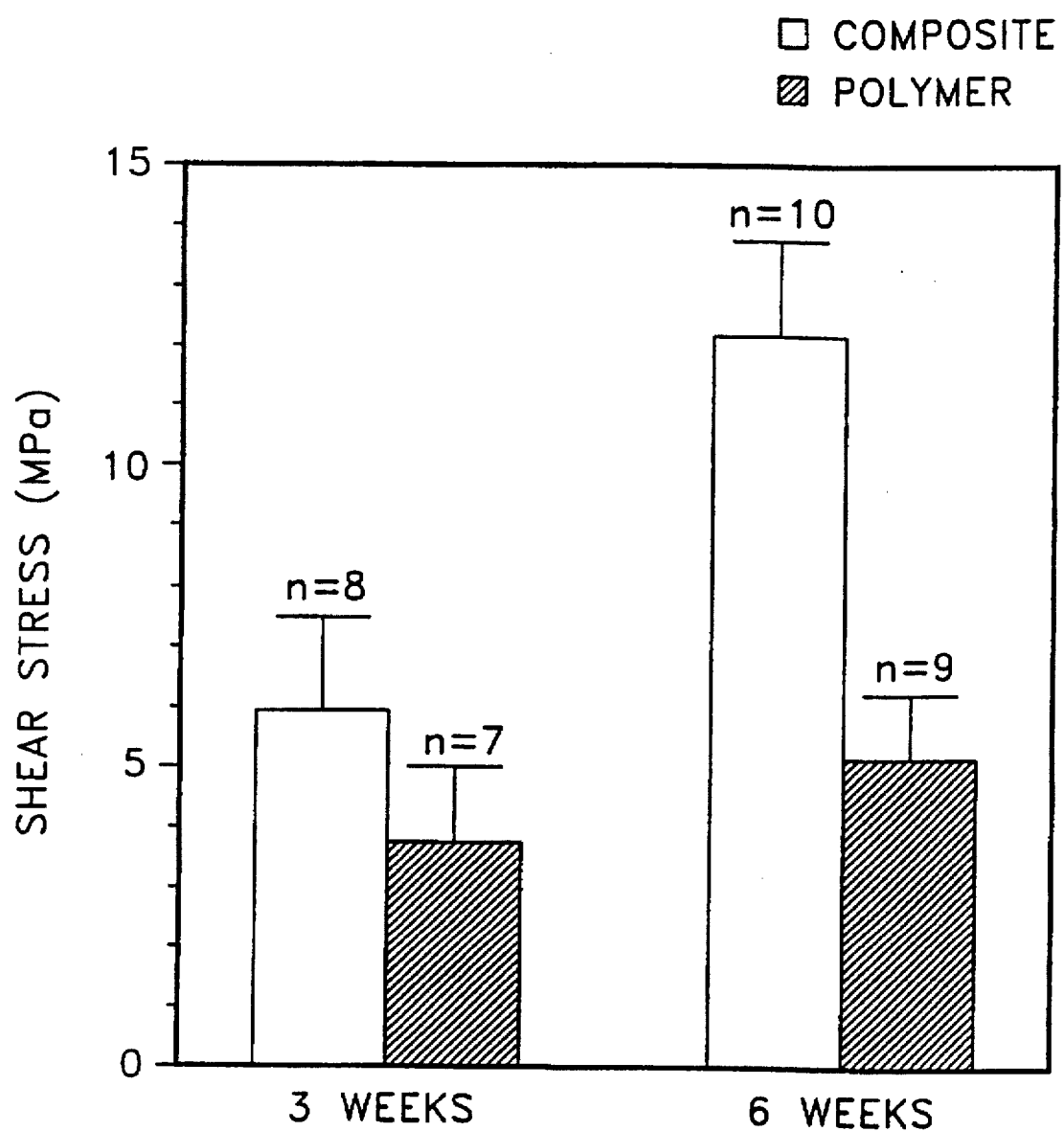
FIG. 8 depicts the interfacial bond strength of a composite implant and a polymer implant at three weeks and six weeks implantation time.

Interfacial bond strength values are shown in FIG. 8. The mean shear strength between the bioactive glass fiber/polymer composite and bone tissue after six weeks was 12.4 MPa (1798 psi), compared to the control polymer which had a mean value of 5.2 MPa (358 psi). Interfacial bond strengths for the polymer at the two time points did not change significantly.

After retrieval, the untested bone/implant samples were dehyrated in a solution of one part formaldehyde, neutralized with $CaCO_3$ (50 g/L) and two parts 80% ethanol for a minimum of 24 hours. Following fixation, the blocks of tissue were consecutively dehydrated for 24 hours in each 70%, 80%, 90%, and 94% ethanol and for 48 hours in absolute ethanol. The samples were then embedded in methylmethacrylate by immersing in pure methylmethacrylate for six days and then in a mixture of methylmethacrylate with benzoylperoxide and plastoid N for three days. The samples were cured in an oven at 60° C.

Embedded samples were sectioned and ground with a final polish using 600 grid SiC paper. Half of the sections were stained with Stevenel's blue and Van Gieson's picrofuchsin. Stained sections were examined using the light microscope and unstained sections were sputter coated with carbon and analyzed using SEM/EDXA.

The histological sections were quantitatively analyzed by measuring bone contact at implant surface as a percentage of linear area. The measurements from the various sections for each specimen were averaged to obtain one data point per specimen. The bone contact measurements between the polymer and composite at both time points were compared using two-way analysis of variance with replication and the pairwise comparisons were analyzed using a t-test with Bonferroni adjustment (Systat, Systat, Inc.). Within the six week data set, a regression analysis was performed to determine the relationship between bone contact area and interfacial bond strength for both the polymer and composite implants.

Figure 9:
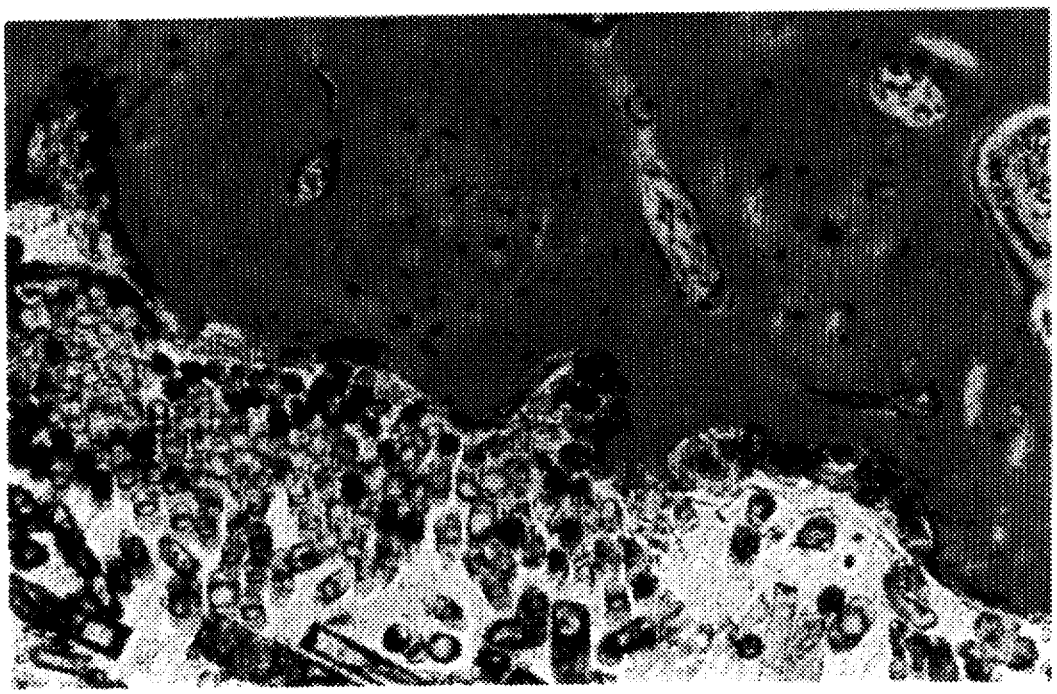
FIG. 9 is a photomicrograph of the composite implant/bone interface after six weeks implantation, 200× magnification.
Figure 10:
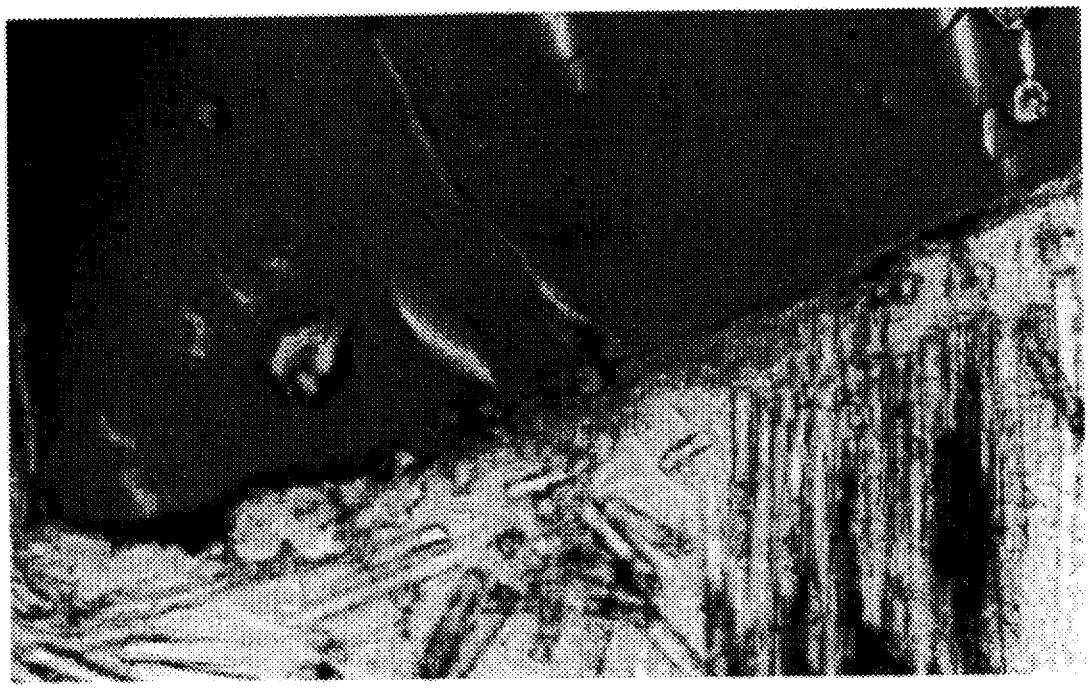
FIG. 10 is a photomicrograph of the composite implant/bone interface after three weeks implantation, 200× magnification.

The composite material showed very close apposition to bone tissue at both three and six weeks. As seen in FIG. 9, by six weeks the bone tissue was well-integrated with the composite material. The bone was directly opposed to both fibers and polymer. The same observation was detected in FIG. 10 where the bone tissue was beginning to interact with the composite fibers after only three weeks. There were no distinct differences between the three and six week composite sections as observed using light microscopy.

The interface between the polymer and bone was sometimes interposed by fibrous tissue, but often had spots of apparent bone contact. There was no interdigitation between the bone apposed to the polymer as was typically observed with the composite implants. As for the composites, there were no distinct differences between the three and six week polymer sections as observed using light microscopy.

Figure 11:
FIG. 11 is a scanning electron micrograph of the composite implant/bone interface after six weeks implantation.

Scanning electron microscopy revealed bone tissue in direct apposition to bioactive glass fibers after six weeks of implantation. Morphologically, it appears as if a fiber in FIG. 11 is being incorporated into the bony matrix. EDXA indicated that both the fiber area and the web consisted of calcium and phosphorous. This is most likely an example of a fiber which has partially resorbed, allowing the bone to infiltrate the region.

The interface measured between the polymer region of composite material which was implanted for three weeks and bone tissue was approximately 3–4 µm thick. Calcium, phosphorous, sulfur, and silicon were detected in this layer by EDXA. Silicon was not detected on the bone or polymer side of the interface. This same observation was made on a six week composite specimen, where the interfacial layer was 4–5µm thick.

The areas where glass fibers were exposed to bone tissue revealed bone tissue adjacent to the glass fibers without an interposing fibrous tissue layer. A calcium-phosphate-rich reaction layer was detected on the surface of glass fibers which were in contact with bone tissue. However, a distinct region of a silica-rich layer was not detected through SEM/EDXA analysis. This may be due to the detection limit of the EDXA corresponding to the thickness of reaction layer to be detected. Although the thickness of the weak silica-gel layer cannot be quantified, it can be deduced that the layer may have been no thicker than the spatial resolution of the EDXA technique (approximately 2 µm). Previous studies of bioactive glass composite show silica-gel thickness layers to be one to two orders of magnitude greater than this (Van Hove et al., 1993, supra) even at reduced rates of reactions. It has been hypothesized that a reduction in the thickness of the weak silica-gel layer will lead to increased bond strength between bioactive glass and bone (Van Hove et al., 1993, supra).

The reduced rate of reactivity, resultant thickness of the reaction layer, resultant increase in apposition of bone, and concomitant bond strength are all related to the glass composition, more specifically, the $Al_2O_3$ content.

Based upon the foregoing, it will be realized that a number of embodiments of the present invention beyond those discussed in detail above are possible. Such embodiments, however, will still employ the spirit of the present invention and, accordingly, reference should be made to the appended claims in order to determine the full scope of the present invention.

What is claimed is:

1. A biocompatible composite of tows of bone bioactive fibers comprising at least 19% $Na_2O$ by mole and greater than 0.2% $Al_2O_3$ by mole, said tows of bioactive fibers intermingled with tows of structural fibers in a nonbioabsorbable polymeric matrix.

2. The composite of claim 1, wherein the bone bioactive fibers are arranged in a predetermined distribution and a section of a surface of the composite to be affixed to bone is comprised of about 30% or more bone bioactive fibers.

3. The composite of claim 1 wherein the structural fiber is a carbon fiber.

4. The composite of claim 1 wherein the polymeric material is chosen from the group consisting of: polysulfone; PEEK; and PEKK.

5. The composite of claim 1, wherein the bone bioactive fibers comprise 40–60% $SiO_2$, 19–30% $Na_2O$, 10–21% CaO, 0–4% $P_2O_5$, and 0.2–1% $Al_2O_3$ by mole.

6. The composite of claim 1, wherein the bone bioactive fibers comprise 45–55% $SiO_2$, 19–30% $Na_2O$, 15–20% CaO, 0–3% $P_2O_5$, and 0.2–1% $Al_2O_3$ by mole.

7. The composite of claim 1, further comprising a modifier selected from the group consisting of $K_2O$, MgO, and $F_2$.

8. The composite of claim 1 wherein the bone bioactive fibers have a diameter of from about 5 to about 25 microns.

* * * * *